(12) United States Patent
Bordoloi et al.

(10) Patent No.: US 8,337,881 B2
(45) Date of Patent: Dec. 25, 2012

(54) CYANOACRYLATE MONOMER FORMULATION CONTAINING DIIODOMETHYL-P-TOLYLSULFONE

(75) Inventors: Binoy K. Bordoloi, Bridgewater, NJ (US); Shubhangi R. Bhende, Edison, NJ (US)

(73) Assignee: Ethicon, Inc., Somerville, NJ (US)

( * ) Notice: Subject to any disclaimer, the term of this patent is extended or adjusted under 35 U.S.C. 154(b) by 1740 days.

(21) Appl. No.: 10/918,891

(22) Filed: Aug. 16, 2004

(65) Prior Publication Data

US 2005/0053578 A1    Mar. 10, 2005

Related U.S. Application Data

(60) Provisional application No. 60/501,100, filed on Sep. 8, 2003.

(51) Int. Cl.
*A61K 9/00* (2006.01)
*A61K 31/74* (2006.01)
*A61K 31/795* (2006.01)

(52) U.S. Cl. ............ 424/443; 424/78.27; 424/78.35

(58) Field of Classification Search .......... None
See application file for complete search history.

(56) References Cited

U.S. PATENT DOCUMENTS

| | | | |
|---|---|---|---|
| 2,721,858 A | 10/1955 | Joyner et al. | |
| 3,254,111 A | 5/1966 | Hawkins et al. | |
| 3,995,641 A | 12/1976 | Kroenthal et al. | |
| 4,364,876 A | 12/1982 | Kimura et al. | |
| 5,254,132 A * | 10/1993 | Barley et al. | 606/214 |
| 5,585,407 A * | 12/1996 | Patel et al. | 514/772.6 |
| 5,783,177 A * | 7/1998 | Greff et al. | 424/78.17 |
| 5,829,442 A * | 11/1998 | Cox et al. | 128/849 |
| 5,902,594 A | 5/1999 | Greff et al. | |
| 5,928,611 A | 7/1999 | Leung | |
| 5,981,621 A | 11/1999 | Clark et al. | |
| 6,086,906 A | 7/2000 | Greff et al. | |
| 6,090,397 A | 7/2000 | Lee et al. | |
| 6,214,332 B1 | 4/2001 | Askill et al. | |
| 6,216,699 B1 | 4/2001 | Cox et al. | |
| 6,433,096 B1 * | 8/2002 | Hickey et al. | 525/244 |
| 6,475,502 B1 | 11/2002 | Lee et al. | |
| 6,767,552 B2 | 7/2004 | Narang | |
| 2002/0044956 A1 * | 4/2002 | Campbell | 424/435 |
| 2003/0007947 A1 | 1/2003 | Narang | |
| 2003/0007948 A1 | 1/2003 | Hedgpeth | |
| 2003/0082116 A1 | 5/2003 | Badejo et al. | |
| 2006/0093572 A1 * | 5/2006 | Bordoloi et al. | 424/78.27 |

FOREIGN PATENT DOCUMENTS

EP    0 812 893 A2 * 12/1997
WO    WO 00/35276 A1   6/2000

OTHER PUBLICATIONS

International Search Report dated Feb. 4, 2005, for international application PCT/US2004/026544.
Bhende, S. et al 'In Vitro Assessment of Microbial Barrier Properties of Dermabond® Topical Skin Adhesive' Surgical Infections, vol. 3, No. 3, 2002, pp. 251-257.

* cited by examiner

*Primary Examiner* — Robert A Wax
*Assistant Examiner* — Jeffrey T Palenik
(74) *Attorney, Agent, or Firm* — David R. Crichton

(57) ABSTRACT

A polymerizable antimicrobial formulation for forming a wound closure adhesive comprising cyanoacrylate monomer and diiodomethyl-p-tolylsulfone; and a method for closing the approximated edges of a wound with a polymeric film that substantially inhibits the growth of microorganisms, where the polymeric film is formed by use of the polymerizable antimicrobial formulation.

7 Claims, No Drawings

CYANOACRYLATE MONOMER FORMULATION CONTAINING DIIODOMETHYL-P-TOLYLSULFONE

CROSS-REFERENCE TO RELATED APPLICATION

This application claims priority from U.S. Provisional Application Ser. No. 60/501,100, filed on 8 Sep. 2003.

BACKGROUND

Polymerizable cyanoacrylate monomer formulations have been disclosed for a variety of topical uses. Specifically, such formulations have been used as an alternate or an adjunct to surgical sutures and/or staples in wound closure, by forming a polymeric film over the approximated edges of a wound or an incision. Antimicrobial agents may be incorporated into cyanoacrylate monomer formulations in an effort to improve the microbial barrier properties of the resultant polymeric film. However, it is critical that the antimicrobial agent does not cause premature polymerization of the cyanoacrylate monomer formulation when it is desirable for the formulation to be stable over extended periods of time, for use at a later date, i.e., polymerization at a later date. Additionally, the antimicrobial agent must not interfere with the polymerization when the cyanoacrylate monomer formulation is applied to, for example, the approximated edges of a wound. Additionally, the antimicrobial agent must not have any detrimental effect to the mechanical strength of the cyanoacrylate monomer formulation. Finally, the antimicrobial agent must be capable of being released from the polymeric film in sufficient amounts for the agent to be effective.

In this regard, U.S. Pat. No. 6,214,332 describes the compatibility of cyanoacrylate monomers with various antimicrobial agents, such as polyvinylpyrollidone-iodine, silver nitrate, hexachlorophene, merbromin, tetracycline-HCl, tetracycline hydrate and erythromycin. This reference indicates that polyvinylpyrollidone-iodine in solid form produces a cyanoacrylate monomer formulation that is stable for 8 weeks when stored at room temperature, polymerizes to form a polymeric film within 30 seconds, and exhibits an antimicrobial effect.

However, many conventional antimicrobial agents are unsuitable for use in cyanoacrylate monomer formulations due to their inability to satisfy one or more of the criteria described above. For example, although quaternary ammonium salts are commonly used antimicrobial agents, they are also known to initiate polymerization of cyanoacrylate monomers, as described in U.S. patent application Ser. No. 2003/0007948 A, as well as U.S. Pat. Nos. 5,928,611 and 6,767,552. Therefore, it is undesirable to use a quaternary ammonium salt as an antimicrobial agent in a cyanoacrylate monomer formulation when the formulation is required to be stable over extended periods of time.

The use of diiodomethyl-p-tolylsulfone as an antimicrobial agent is desirable because it is a broad spectrum antimicrobial agent. For example, blends of diiodomethyl-p-tolylsulfone, such as Amical-48 (commercially available from Dow), and acrylic hot melt adhesive polymers have been reported in U.S. Pat. No. 6,216,699, for use in surgical incise drapes having antimicrobial properties. Such blends were reported to indicate zones of inhibition against several organisms including S. aureus, E. coli, P. aeruginosa, K. pneumoniae, P. cepacia, E. cloacae, S. marcescens, S. pyogenes, E. faecalis-Vancomycin Resistant, C. albicans and B. subtilis. However, use of diiodomethyl-p-tolylsulfone in a formed polymer or by direct mixing in the polymer melt does not ensure that diiodomethyl-p-tolylsulfone is suitable for use with prepolymeric compositions such the cyanoacrylate monomer formulations described herein.

Therefore, it is desirable to have a stable formulation of cyanoacrylate monomer and diiodomethyl-p-tolylsulfone, where the diiodomethyl-p-tolylsulfone does not cause premature polymerization of the cyanoacrylate monomer formulation when it is desirable for the formulation to be stable over extended periods of time, for use at a later date, i.e., polymerization at a later date; the diiodomethyl-p-tolylsulfone does not interfere with the polymerization when the cyanoacrylate monomer formulation is applied to, for example, the approximated edges of a wound; and the diiodomethyl-p-tolylsulfone is capable of being released from the polymeric film in sufficient amounts to be effective.

SUMMARY OF THE INVENTION

Described herein is a polymerizable antimicrobial formulation comprising monomeric cyanoacrylate and diiodomethyl-p-tolylsulfone, that may be used to form a wound closure adhesive.

DETAILED DESCRIPTION

The present invention is directed to a polymerizable antimicrobial formulation comprising a cyanoacrylate monomer and diiodomethyl-p-tolylsulfone, that forms a polymeric film that is capable of functioning as a wound closure adhesive, wherein the microbial barrier properties of the polymeric film are improved by incorporation of diiodomethyl-p-tolylsulfone therein.

Preferred monomers of formula (I) for use in this invention are alpha-cyanoacrylates. These monomers are known in the art and have the formula

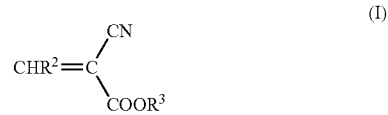

(I)

wherein $R^2$ is hydrogen and $R^3$ is a hydrocarbyl or substituted hydrocarbyl group; a group having the formula —$R^4$—O—$R^5$—O—$R^6$, wherein $R^4$ is a 1,2-alkylene group having 2-4 carbon atoms, $R^5$ is an alkylene group having 2-4 carbon atoms, and $R^6$ is an alkyl group having 1-6 carbon atoms; or a group having the formula

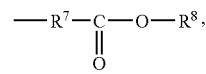

wherein $R^7$ is

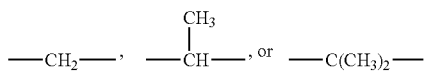

and $R^8$ is an organic radical.

Examples of suitable hydrocarbyl and substituted hydrocarbyl groups include straight chain or branched chain alkyl groups having 1-16 carbon atoms; straight chain or branched chain $C_1$-$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic radical $R^8$ may be substituted or unsubstituted and may be straight chain, branched or cyclic, saturated, unsaturated or aromatic. Examples of such organic radicals include $C_1$-$C_8$.alkyl radicals, $C_2$-$C_8$ alkenyl radicals, $C_2$-$C_8$ alkynyl radicals, $C_3$-$C_{12}$ cycloaliphatic radicals, aryl radicals such as phenyl and substituted phenyl and aralkyl radicals such as benzyl, methylbenzyl and phenylethyl. Other organic radicals include substituted hydrocarbon radicals, such as halo(e.g., chloro-, fluoro- and bromo-substituted hydrocarbons) and oxy-(e.g., alkoxy substituted hydrocarbons) substituted hydrocarbon radicals. Preferred organic radicals are alkyl, alkenyl and alkynyl radicals having from 1 to about 8 carbon atoms, and halo-substituted derivatives thereof. Particularly preferred are alkyl radicals of 4 to 6 carbon atoms.

In the cyanoacrylate monomer of formula (I), $R^3$ is preferably an alkyl group having 1-10 carbon atoms or a group having the formula —$AOR^9$, wherein A is a divalent straight or branched chain alkylene or oxyalkylene radical having 2-8 carbon atoms, and $R^9$ is a straight or branched alkyl radical having 1-8 carbon atoms. Examples of groups represented by the formula —$AOR^9$ include 1-methoxy-2-propyl, 2-butoxy ethyl, isopropoxy ethyl, 2-methoxy ethyl, and 2-ethoxy ethyl.

The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate.

The alpha-cyanoacrylates of formula (I) can be prepared according to methods known in the art. Reference is made, for example, to U.S. Pat. Nos. 2,721,858 and 3,254,111, each of which is hereby incorporated by reference herein. For example, the alpha cyanoacrylates can be prepared by reacting an alkyl cyanoacetate with formaldehyde in a non-aqueous organic solvent and in the presence of a basic catalyst, followed by pyrolysis of the anhydrous intermediate polymer in the presence of a polymerization inhibitor. The alpha-cyanoacrylate monomers prepared with low moisture content and essentially free of impurities are preferred for biomedical use.

The alpha-cyanoacrylates of formula (I) wherein $R^3$ is a group having the formula —$R^4$—O—$R^5$—O—$R^6$ can be prepared according to the method disclosed in U.S. Pat. No. 4,364,876 to Kimura et al., which is hereby incorporated by reference herein. In the Kimura et al. method, the alpha-cyanoacrylates are prepared by producing a cyanoacetate by esterifying cyanoacetic acid with an alcohol or by transesterifying an alkyl cyanoacetate and an alcohol; condensing the cyanoacetate and formaldehyde or paraformaldehyde in the presence of a catalyst at a molar ratio of 0.5-1.5:1, preferably 0.8-1.2:1, to obtain a condensate; depolymerizing the condensation reaction mixture either directly or after removal of the condensation catalyst to yield crude cyanoacrylate; and distilling the crude cyanoacrylate to form a high purity cyanoacrylate.

The alpha-cyanoacrylates of formula (I) wherein $R^3$ is a group having the formula

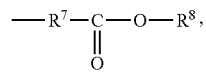

can be prepared according to the procedure described in U.S. Pat. No. 3,995,641 to Kronenthal et al., which is hereby incorporated by reference herein. In the Kronenthal et al. method, such alpha-cyanoacrylate monomers are prepared by reacting an alkyl ester of an alpha-cyanoacrylic acid with a cyclic 1,3-diene to form a Diels-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Examples of monomers of formula (I) include cyanopentadienoates and alpha-cyanoacrylates of the formula:

(II)

wherein Z is —CH=$CH_2$ and $R^3$ is as defined above. The monomers of formula (II) wherein $R^3$ is an alkyl group of 1-10 carbon atoms, i.e., the 2-cyanopenta-2,4-dienoic acid esters, can be prepared by reacting an appropriate 2-cyanoacetate with acrolein in the presence of a catalyst such as zinc chloride.

According to the present invention, the components in the cyanoacrylate monomer formulation include, but are not limited to free-radical stabilizers, anionic stabilizers, plasticizers, thickeners etc. The details are described in U.S. Pat. Nos. 5,981,621, and 6,433,096 the contents each of which is incorporated by reference herein in its entirety.

The cyanoacrylate monomer formulation may optionally also include at least one plasticizing agent that imparts flexibility to the polymeric film formed from the monomer. The plasticizing agent preferably contains little or no moisture and should not significantly affect the stability or polymerization of the monomer. Such plasticizers are useful for closure or covering of wounds, incisions, abrasions, sores or other applications where flexibility of the adhesive is desirable.

Examples of suitable plasticizers include tributyl citrate, acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate and mixtures thereof. Preferred plasticizers are tributyl citrate and acetyl tributyl citrate.

The addition of plasticizing agents in amounts ranging from about 0.5 wt. % to about 25 wt. %, or from about 1 wt. % to about 20 wt. %, or from about 3 wt. % to about 15 wt. % or from about 5 wt. % to about 7 wt. % provides increased elongation and toughness of the polymeric film over polymeric film not having plasticizing agents.

The thickening agents may be selected from among known thickeners, including, but not limited to, poly(2-ethylhexyl methacrylate), poly(2-ethylhexyl acrylate) and cellulose acetate butyrate. Suitable thickeners include, for example, polycyanoacrylates, polyoxalates, lactic-glycolic acid copolymers, polycaprolactone, lactic acid-caprolactone copolymers, poly(caporolactone+DL-lactide+glycolide), polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(butylmethacrylate) and poly(butylacrylate), also copolymers of various acrylate and methacrylate monomers, such as poly(butylmethacrylate-co-methylmethacrylate). Biodegradable polymer thickeners are preferred for some uses such as some surgical uses. Preferably, the thickening agent is soluble in a cyanoacrylate monomer formulation at room temperature (i.e. 20-25° C.) so that it may be added to the cyanoacrylate monomer formulation without excessive heating of the cyanoacrylate monomer formulation and remain uniformly combined in the cyanoacrylate monomer formulation.

The amount of thickening agent that is added to the cyanoacrylate monomer formulation depends upon the molecular weight of the thickening agent. The thickening agent preferably comprises from about 0.5-25.0% by weight of the cyanoacrylate monomer formulation. In preferred embodiments, the thickening agent comprises from about 1.0-10.0%, more preferably 1.0-5.0%, of the cyanoacrylate monomer formulation. In embodiments, the thickening agent has a high molecular weight, preferably at least 100,000, or at least 500,000 or at least 1,000,000. The thickening agent is selected such that it is compatible with the monomer (i.e., does not adversely affect polymerization, bond strength or stability). The amount of thickening agent to be used can be determined by one of ordinary skill in the art using known techniques without undue experimentation.

In embodiments, the cyanoacrylate monomer formulation has a viscosity of about 5-500 centipoise, preferably 30-400 centipoise, as measured with a Brookfield Viscometer at 25° C.

The cyanoacrylate monomer formulation may also optionally include both at least one anionic vapor phase stabilizer and at least one anionic liquid phase stabilizer. These stabilizing agents inhibit premature polymerization. Such stabilizing agents may also include mixtures of anionic stabilizing agents and radical stabilizing agents. Any mixture of stabilizers is included as long as the mixture does not inhibit polymerization of the monomer upon contact with an initiator and is compatible with the selected thickener.

Examples of suitable radical stabilizing agents include hydroquinone, hydroquinone monomethyl ether, catechol, pyrogallol, benzoquinone, 2-hydroxybenzoquinone, p-methoxy phenol, t-butyl catechol, butylated hydroxy anisole, butylated hydroxy toluene, and t-butyl hydroquinone.

The anionic vapor phase stabilizers may be selected from among known stabilizers, including, but not limited to, sulfur dioxide, boron trifluoride, and hydrogen fluoride. The amount of anionic vapor phase stabilizer that is added to the cyanoacrylate monomer formulation depends on the identity of the liquid phase stabilizer(s) chosen in combination with it, the monomer to be stabilized, as well as the packaging material to be used for the cyanoacrylate monomer formulation. Preferably, each anionic vapor phase stabilizer is added to give a concentration of less than 200 parts per million (ppm). In preferred embodiments, each anionic vapor phase stabilizer is present from about 1 to 200 ppm, more preferably from about 10 to 75 ppm, even more preferably from about 10 to 50 ppm, and most preferably from 10 to 20 ppm. The amount to be used can be determined by one of ordinary skill in the art using known techniques without undue experimentation.

In embodiments, the vapor phase comprises, among other things, an anionic stabilizer that is sulfur dioxide. In embodiments, the vapor phase comprises, among other things, a stabilizer that is boron trifluoride or hydrogen fluoride. A combination of sulfur dioxide and boron trifluoride or hydrogen fluoride is preferable in some embodiments.

In embodiments, the liquid phase anionic stabilizer is a very strong acid. As used herein, a very strong acid is an acid that has an aqueous pKa of less than 1.0. Suitable very strong acidic stabilizing agents include, but are not limited to, very strong mineral and/or oxygenated acids. Examples of such very strong acids include, but are not limited to, sulfuric acid (pKa −3.0 to −5.2) and perchloric acid (pKa −5.0). In embodiments, the very strong acid liquid phase anionic stabilizer is added to give a final concentration of 1 to 200 ppm. Preferably, the very strong acid liquid phase anionic stabilizer is present in a concentration of from about 5 to 80 ppm, more preferably 10 to 40 ppm. The amount of very strong acid liquid phase anionic stabilizer to be used can be determined by one of ordinary skill in the art without undue experimentation. Preferably, the very strong acid liquid phase anionic stabilizer is sulfuric acid, perchloric acid, or chlorosulfonic acid. More preferably, the very strong acid liquid phase anionic stabilizer is sulfuric acid.

In embodiments, sulfur dioxide is used as a vapor phase anionic stabilizer and sulfuric acid is used as a liquid phase anionic stabilizer. Combinations of at least one vapor phase stabilizer and at least one liquid phase anionic stabilizer are preferred. For example, combinations of sulfur dioxide and sulfuric acid, sulfur dioxide and perchloric acid, sulfur dioxide and chlorosulfonic acid, boron trifluoride and sulfuric acid, boron trifluoride and perchloric acid, boron trifluoride and chlorosulfonic acid, boron trifluoride and methanesulfonic acid, hydrogen fluoride and sulfuric acid, hydrogen fluoride and perchloric acid, hydrogen fluoride and chlorosulfonic acid, and hydrogen fluoride and methanesulfonic acid can be used. A combination of boron trifluoride, sulfur dioxide, and sulfuric acid can also be used, among other combinations. The two types of anionic stabilizers are chosen in conjunction such that the stabilizers are compatible with the chosen adhesive cyanoacrylate monomer formulation and each other stabilizer, as well as with the packaging material and the equipment used to make and package the cyanoacrylate monomer formulation. In other words, the combination of vapor phase stabilizer(s), liquid phase stabilizer(s), and monomer should be such that a stabilized, substantially unpolymerized adhesive cyanoacrylate monomer formulation is present after packaging.

The cyanoacrylate monomer formulation may also optionally include at least one other anionic stabilizing agent that inhibits premature polymerization. These agents are herein referred to as secondary anionic active agents to contrast them with the strong or very strong liquid phase anionic stabilizers, which are referred to herein below as "primary" anionic stabilizers. The secondary anionic active agents can be included in the cyanoacrylate monomer formulation to adjust its cure speed.

The secondary anionic active agent would normally be an acid with a higher pKa than the primary anionic stabilizing agent and may be provided to more precisely control the cure speed and stability of the adhesive, as well as the molecular weight of the cured adhesive. Any mixture of primary anionic stabilizers and secondary active agents is included as long as the chemistry of the cyanoacrylate monomer formulation is not compromised and the mixture does not significantly inhibit the desired polymerization of the cyanoacrylate monomer formulation. Furthermore, the mixture should not, in medical cyanoacrylate monomer formulation, show unacceptable levels of toxicity.

Suitable secondary anionic active agents include those having aqueous pKa ionization constants ranging from 2 to 8, preferably from 2 to 6, and most preferably from 2 to 5. Examples of such suitable secondary anionic stabilizing agents include, but are not limited to, phosphoric acid (pKa 2.2), organic acids, such as acetic acid (pKa 4.8), benzoic acid (pKa 4.2), chloroacetic acid (pKa 2.9), cyanoacetic acid, and mixtures thereof. Preferably these secondary anionic stabilizing agents are organic acids, such as acetic acid or benzoic acid. In embodiments, the amount of acetic acid and/or benzoic acid is about 25-500 ppm. The concentration of acetic acid is typically 50-400 ppm, preferably 75-300 ppm, and more preferably 100-200 ppm. When using a stronger acid such as phosphoric acid, a concentration of 20-100 ppm, preferably 30-80 ppm, and more preferably 40-60 ppm may be utilized.

As discussed above, blends of diiodomethyl-p-tolylsulfone and acrylic hot melt adhesive polymers were reported to indicate zones of inhibition against several organisms including S. aureus, E. coli, P. aeruginosa, K. pneumoniae, P. cepacia, E. cloacae, S. marcescens, S. pyogenes, E. faecalis-Vancomycin Resistant, C. albicans and B. subtilis. Therefore, this antimicrobial agent is a broad spectrum antimicrobial agent, for example, having a minimum inhibitory concentration against C. albicans of about 5 ppm.

Minimum inhibitory concentration is the lowest concentration that prevents the development of visible growth after a period of incubation. Minimum bactericidal concentration is the lowest concentration that achieves a 1000 fold or greater reduction in the original bacterial inoculum. The minimum inhibitory concentration (MIC) and minimum bactericidal concentration (MBC) is evaluated using tube dilution procedure.

Zone of inhibition testing is a commonly used microbiological test to evaluate antimicrobial effect of a diffusible agent against microbial strains of interest. As the agent diffuses away from the disk, the concentration decreases logarithmically. The sensitivity of the organism to the agent is judged by the appearance and size of a zone where no growth occurs, the zone of inhibition. Areas devoid of growth around the material represent the zone of inhibition, i.e., the concentration of the antimicrobial agent is greater than the minimum inhibitory concentration (MIC) for the particular challenge organism. The clear area around the material indicates that the challenge organisms were killed or inhibited by the diffusible agent.

Diiodomethyl-p-tolylsulfone (DIMPTS) is soluble in cyanoacrylate monomer at least up to 15,000 ppm (wt./wt.). Accordingly, formulations may herein have a concentration of diiodomethyl-p-tolylsulfone ranging from about 500 (0.05%) to about 10,000 ppm (1.00%), preferably from about 700 (0.07%) to about 7,000 ppm (0.70%), more preferably the concentration of diiodomethyl-p-tolylsulfone is about 2800 ppm (0.28%).

The cyanoacrylate monomer formulation may be packaged in any type of suitable container fabricated from materials including, but not limited to, glass, plastic, metal packages, and film-formed packages. Suitable containers are those into which the cyanoacrylate monomer formulation can be dispensed and sterilized without unacceptable damage to, or degradation of, the container or the components of the cyanoacrylate monomer formulation. Glass is especially preferred when sterilization is achieved with dry heat because of the lack of stability of many plastics at the temperatures used for dry heat sterilization (typically at least 160° C.). Examples of types of containers include, but are not limited to, ampoules, vials, syringes, pipettes, and the like. In a preferred embodiment, the container comprises a sealable container.

For biomedical applications, the cyanoacrylate monomer formulation according to the invention may be sterilized. The sterilization can be accomplished by techniques known to the skilled artisan, and is preferably accomplished by methods including, but not limited to, chemical, physical, and irradiation methods. Examples of chemical methods include, but are not limited to, exposure to ethylene oxide or hydrogen peroxide vapor. Examples of physical methods include, but are not limited to, sterilization by heat (dry or moist). Examples of irradiation methods include, but are not limited to, gamma irradiation, electron beam irradiation, and microwave irradiation. Preferred methods are dry and moist heat sterilization and electron beam sterilization. In embodiments where a cyanoacrylate monomer formulation is to be used for medical applications, the sterilized cyanoacrylate monomer formulation must show low levels of toxicity to living tissue during its useable life.

During use, the cyanoacrylate monomer formulation containing diiodomethyl-p-tolylsulfone may form a biocompatible film across abutted tissue surfaces in the steps as follows: (a) holding together at least two tissue surfaces to form abutted tissue surfaces, (b) applying across the abutted tissue surfaces an adhesive biocompatible cyanoacrylate monomer formulation, and (c) allowing the cyanoacrylate monomer formulation to polymerize and form a biocompatible film on the abutted tissue surfaces.

When the cyanoacrylate monomer formulation is cured to a film on an incision on a latex substrate, the mechanical strength of the construction formed with the film and the latex substrate may be tested by a burst test method as described below. The polymeric film preferably has a burst strength ranging from at least about 10 to 20 psi and more preferably at least about 12 to 20 psi.

EXAMPLES

The invention is further illustrated by the following non-limiting examples. The following examples demonstrate that a commercially available, stabilized formulation of 2-octyl cyanoacrylate (sold as DERMABOND® Topical Skin Adhesive by Ethicon, Inc., Somerville, N.J.) that includes a sufficient quantity of diiodomethyl-p-tolylsulfone is stable after heat sterilization and/or heat aging for extended periods of time. The sterilized or heat aged monomer samples may be polymerized under appropriate conditions producing a polymeric film that exhibits antimicrobial activity in a standard antimicrobial challenge.

Example 1

Nine acid washed oven-dried boro-silicate (USP-1) glass ampoules were charged with various concentrations of diiodomethyl-p-tolylsulfone (DIMPTS) in 2-octylcyanoacrylate.

1.5028 g of DERMABOND® Topical Skin Adhesive and 0.0012 g of solid diiodomethyl-p-tolylsulfone were placed in an ampoule. The ampoule was sufficiently agitated to dissolve the diiodomethyl-p-tolylsulfone in the 2-octylcyanoacrylate. 0.4966 g of the resultant solution was placed in ampoule #1; 0.4760 g of the solution was placed in ampoule #2, and the original ampoule, ampoule #3 was left with 0.5302 g.

1.5090 g of DERMABOND® Topical Skin Adhesive and 0.0025 g of solid diiodomethyl-p-tolylsulfone were placed in an ampoule. The ampoule was sufficiently agitated to dissolve the diiodomethyl-p-tolylsulfone in the 2-octylcyanoacrylate. 0.5103 g of the resultant solution was placed in ampoule #4; 0.4991 g of the solution was placed in ampoule #5, and the original ampoule, ampoule #6 was left with 0.4996 g.

1.5134 g of DERMABOND® Topical Skin Adhesive and 0.0046 g of solid diiodomethyl-p-tolylsulfone were placed in an ampoule. The ampoule was sufficiently agitated to dissolve the diiodomethyl-p-tolylsulfone in the 2-octylcyanoacrylate. 0.5100 g of the resultant solution was placed in ampoule #7; 0.4978 g of the solution was placed in ampoule #8, and the original ampoule, ampoule #9 was left with 0.5056 g.

Ampoules #1, #4, and #7 were exposed to dry heat for 65 minutes at 160° C.

Ampoules #2, #5, and #8 were exposed gamma irradiation at 15 kGy.

Ampoules #3, #6, and #9 were exposed gamma irradiation at 20 kGy.

TABLE I

| Sample # | DIMPTS conc. (ppm) in 2-OCA | Sterilization method | Observations |
|---|---|---|---|
| 1 | 700 | Heat @ 160° C./65 min | Colorless ampoule |
| 2 | 700 | Gamma @ 15 kGy | Glass ampoule slightly brown |
| 3 | 700 | Gamma @ 20 kGy | Glass ampoule slightly brown |
| 4 | 1400 | Heat @ 160° C./65 min | Colorless ampoule |
| 5 | 1400 | Gamma @ 15 kGy | Glass ampoule slightly brown |
| 6 | 1400 | Gamma @ 20 kGy | Glass ampoule slightly brown |
| 7 | 2800 | Heat @ 160° C./65 min | Colorless ampoule |
| 8 | 2800 | Gamma @ 15 kGy | Glass ampoule slightly brown |
| 9 | 2800 | Gamma @ 20 kGy | Glass ampoule slightly brown |

After heat exposure @ 160° C. for 65 min, ampoule #1 was noticeably cloudy. Upon inspection 18 hours later, the content of ampoule #1 was still a cloudy solution, somewhat more viscous than previous but still flowed. Upon inspection 84 hours later, the content of ampoule #1 was cloudy, and quite viscous, possibly solidified.

Ampoule #4 was substantially transparent after the heat exposure, but it became a gray color instead of the original purple color of DERMABOND® Topical Skin Adhesive. Ampoule #7 had no apparent change after the heat exposure.

Ampoules #2, #3, #5, #6, #8 and #9 exhibited a glass color change typical of changes induced in boro-silicate glass by the gamma irradiation. Despite this color alteration to the glass ampoule, there was no apparent discoloration of the formulations in these ampoules the day following sterilization. Test results of the samples outlined in example 1 and Table I are shown in example 2 and Table II(B).

Example 2

The antimicrobial efficacy of the formulations described herein was tested against *Staphylococcus aureus* ATCC 6538; *Staphylococcus epidermidis* ATCC 51625 (Methicillin resistant); *Enterococcus faecium* ATCC 700221 (Vancomycin resistant); *Escherichia coli* ATCC 8739; *Pseudomonas aeruginosa* ATCC 9027; and *Candida albicans* ATCC 10231. Cultures of the challenge organisms were grown in 20 ml sterile Trypticase Soy Broth (TSB) for 16-24 hours at 35-37° C.

Trypticase Soy Agar (TSA) plates were used for the assay. A 0.85% saline solution was utilized for dilutions. All media was steam sterilized prior to use. Agar plates were prepared by pouring approximately 20 ml of molten media into sterile disposable petri dishes (100×15 mm). The agar plates were allowed to solidify under a laminar flow hood.

Overnight cultures were vortexed and one 1:100 dilution was prepared to obtain a minimum of $10^4$ colony-forming units (CFU)/ml. The diluted inoculum was spread on the agar plate surface using sterile cotton swabs. Care was taken to cover the entire agar surface uniformly. Plates were allowed to air dry for 30 minutes.

Twenty micro liters of test sample were added to the center of the inoculated plate. Two drops of control sample were expressed onto separate TSA plates. Test sample drops were not spread manually and were allowed to polymerize on the plates to form a thin film. The plates were incubated at 35-37° C. for 24 hours. Plates were examined for the zones of inhibition resulting from the diffusion of the active agents out of the product and into the agar medium. The zone of inhibition was measured in millimeters (mm) from the edge of the film to the edge where the clear zone ends. The antimicrobial efficacy of the composition is described in terms of zone of inhibition in Table II (B).

The effectiveness of the antimicrobial property of pure DIMPTS is described in terms of minimum inhibitory concentration (MIC) and minimum bactericidal concentration (MBC) in Table II (A).

TABLE II(A)

Preliminary Evaluation of DIMPTS for Minimum Inhibitory Concentrations and Minimum Bactericidal Concentrations (MIC's/MBC's)

| | DIMPTS (ppm) | |
|---|---|---|
| Organism | MIC | MBC |
| *Staphylococcus aureus* 6538 | 100 | <250 |
| *Escherichia coli* 8739 | 100 | <250 |
| *Pseudomonas aeruginosa* 9027 | >100 | NA |
| *Enterococcus faecium* 700221 | 50 | NA |
| *Staphylococcus aureus* 33591 | 12.5 | <250 |
| *Staphylococcus epidermidis* 51625 | 25 | <100 |
| *Streptococcus agalactiae* 624 | 50 | 125–250 |
| *Bacillus subtilis* 902173 | 50 | 50–100 |
| *Candida albicans* 10231 | 5 | 10–100 |

Table II(B) reports stability data (mole % monomer) of the cyanoacrylate monomer formulation as determined by NMR and antimicrobial efficacy as determined by zone of inhibition data, for the samples listed in Table I.

TABLE II (B)

Stability (Heat & Gamma) and Average
Zone diameter on TSA plate (mm)
Sample Description

| Challenge Organisms | Organism Type | DERMABOND control | 700 ppm, heat | 1400 ppm, heat | 2800 ppm, heat | 700 ppm, 15 kGy | 1400 ppm, 15 kGy | 2800 ppm, 15 kGy | 700 ppm, 20 kGy | 1400 ppm, 20 kGy | 2800 ppm, 20 kGy |
|---|---|---|---|---|---|---|---|---|---|---|---|
| | | Observation; Stability (% monomer) | | | | | | | | | |
| | | normal viscosity; purple; clear; 95.3% | normal viscosity; purple; clear; 85.3% | normal viscosity; purple; clear; 90.9% | normal viscosity; purple; clear; 93.1% | normal viscosity; purple; clear;*** | normal viscosity; purple; clear; 76.0% | normal viscosity; purple; clear; 82.3% | normal viscosity; purple; clear; 48.3% | normal viscosity; purple; clear; 76.6% | normal viscosity; purple; clear; 80.4% |
| S. aureus | Gram+ | 2 | 4 | 5 | 4 | 7 | 6 | 5 | 7 | 7 | 6 |
| S. epidermidis MRSE | Gram+ | 7 | 5 | 5 | 5* | 9* | 7 | 8 | 8 | 8* | 9* |
| E. faecium VRE | Gram+ | ** | 4* | 4* | 4* | 5 | 6 | 6* | 6 | 7 | 4* |
| E. coli | Gram− | 0 | 0 | 0 | 0 | 1 | 1 | 1 | 1.5 | 1 | 1.5 |
| P. aeruginosa | Gram− | 0 | 0 | 0 | 0 | 0 | 0 | 0 | 0 | 0 | 0 |
| C. albicans | yeast | 0 | 2 | 1 | 5 | 2 | 4 | 5 | 2 | 4 | 9 |

Note:
*1 or 2 colonies seen within the clear zone
**Reduced growth approximately 2 mm surrounding the sample
***sample leaked, test was not performed The formulation containing diiodomethyl-p-tolylsulfone showed substantially increased activity against *Staphylococcus aureus, Staphylococcus epidermidis, Enterococcus faecium* and *Candida albicans* when compared with the control. Activity against *Candida albicans* substantially increases with an increase in the concentration of diiodomethyl-p-tolylsulfone. Radiation sterilized samples of the formulation containing diiodomethyl-p-tolylsulfone showed increased activity against *E.coli* when compared with the control. Heat sterilized formulations containing diiodomethyl-p-tolylsulfone at higher concentration do not show activity against *E.coli*. Formulations containing diiodomethyl-p-tolylsulfone did not display a zone of inhibition around the test film samples when challenged with *Pseudomonas aeruginosa*. However, there was no growth of *Pseudomonas aeruginosa* seen under the test film sample area.

Example 3

Table III lists additional samples (10 to 15) prepared and exposed to several conditions in similar fashion as those in example 1 and Table I. The viscosities listed are determined on a Brookfield Viscometer (Model # DV2 Plus; Spindle # 40, 100 RPM speed, at 25° C.). The percent monomer was determined by NMR (400 mHz) in CDCl$_3$ solution.

TABLE III

| Sample # | DIMPTS concentration (ppm) in DERMABOND ® Topical Skin Adhesive | Sterilization Method (Heat or Gamma) | Visual Observations | Mole % Monomer (by NMR) (n = 1) | Viscosity (CPS) (n = 1) |
|---|---|---|---|---|---|
| Control A | DERMABOND ® Topical Skin Adhesive in original vial | None | Purple liquid/ low viscosity | 95.5 | 6.8 |
| Control B | DERMABOND ® Topical Skin Adhesive in original vial + no DIMPTS | Heat @ 160° C. for 65 min | Glass unchanged, liquid yellow, low viscosity | 78.1% | |
| Control C | DERMABOND ® Topical Skin Adhesive in original vial + no DIMPTS | Gamma @ 20 kGy | Glass slightly brown, liquid purple, low viscosity | 91.0% | |
| 10 | DIMPTS (870 ppm) in DERMABOND ® Topical Skin Adhesive | Heat @ 160° C. for 65 min | Glass unchanged, liquid purple, low viscosity | 88.4% | |

TABLE III-continued

| Sample # | DIMPTS concentration (ppm) in DERMABOND® Topical Skin Adhesive | Sterilization Method (Heat or Gamma) | Visual Observations | Mole % Monomer (by NMR) (n = 1) | Viscosity (CPS) (n = 1) |
|---|---|---|---|---|---|
| 11 | DIMPTS (870 ppm) in DERMABOND® Topical Skin Adhesive | Gamma @ 20 kGy | Glass slightly brown, liquid purple, low viscosity | 85.2% | |
| 12 | DIMPTS (1350 ppm) in DERMABOND® Topical Skin Adhesive | Heat @ 160° C. for 65 min | Glass unchanged, liquid yellow, low viscosity | 80.2% | |
| 13 | DIMPTS (1350 ppm) in DERMABOND® Topical Skin Adhesive | Gamma @ 20 kGy | Glass slightly brown, liquid purple, low viscosity | 83.4% | 20.4 |
| 14 | DIMPTS (2832 ppm) in DERMABOND® Topical Skin Adhesive | Heat @ 160° C. for 65 min | Glass unchanged, liquid purple, low viscosity | 90.8% | 9.6 |
| 15 | DIMPTS (5477 ppm) in DERMABOND® Topical Skin Adhesive | Heat @ 160° C. for 65 min | Glass unchanged, liquid purple, low viscosity | 86.0% | |

Table III indicates that the percent monomer and viscosity of the monomer formulations incorporated with diiodomethyl-p-tolylsulfone (DIMPTS) were consistent with the control material.

Example 4

Cyanoacylate monomer formulation samples made by incorporating 2793 ppm DIMPTS in commercially available DERMABOND® Topical Skin Adhesive were evaluated. Percent monomer as measured by NMR was evaluated under various conditions. Evaluations were made after the sample was prepared at 80° C.; after the sample was prepared and subjected to a heat sterilization cycle (without any aging) at 160° C. for 65 minutes; after the sample was prepared and subjected to aging for 6 days at 80° C. (without a heat sterilization cycle); and after the sample was prepared and subjected to aging for 12 days at 80° C. (without a heat sterilization cycle). The control was commercially available DERMABOND® Topical Skin Adhesive. Table IV displayed the results of sample 16 through 19.

TABLE IV

| Sample # | | | % of monomer (n = 3) | |
|---|---|---|---|---|
| A: control B: compositions | Aging Conditions | Sterilization method | Control (0 ppm) | Compositions (2793 ppm) |
| 16 A-B | 0 day at 80° C. | None | 97.7 | 98.0 |
| 17 A-B | 6 days at 80° C. | None | 92.3 (n = 2) | 91.5 |
| 18 A-B | 12 days at 80° C. | None | 76.1 | 75.9 |
| 19 A-B | None | Heat @ 160° C./ 65 min | 96.6 | 95.7 |

Table IV indicates that a monomer formulation containing 2793 ppm diiodomethyl-p-tolylsulfone demonstrated comparable stability to that of the control sample after sterilization and over varied conditions.

Example 5

Cyanoacylate monomer formulation samples made by incorporating 2834 ppm DIMPTS in commercially available DERMABOND® Topical Skin Adhesive, exposed at several conditions followed by stabilizing treatment with hydroquinone and sulfur dioxide, were evaluated. The stabilizing treatment was conducted in order to maintain the viscosity of the DERMABOND® Topical Skin Adhesive containing 2834 ppm DIMPTS after the heat sterilization cycle described below.

Specifically, DERMABOND® Topical Skin Adhesive having 2834 ppm DIMPTS and 438 ppm hydroquinone were placed in a flask that was washed with 1N sulfuric acid for 3 hours, rinsed with DI water for 3 times and dried overnight at 110° C. Ampoules were then filled with DERMABOND® Topical Skin Adhesive/DIMPTS/hydroquinone and blanketed for 10 second with 250 ppm mixture of sulfur dioxide in nitrogen and immediately sealed. All the ampoules were then heat sterilized at 160° C. for 65 min.

Burst tests were then carried out using a method similar to that used for the Mullen burst. A latex film having an incision length of 1.3 cm in the center of each square was cut into pieces of 10.9 cm$^2$. A Teflon coated low carbon steel mold having a square cutout is placed on a latex square with the incision in the center of the cutout. 50 microliters of cyanoacylate monomer formulation is applied to the latex square using a micropipette. The cyanoacylate monomer formulation is allowed to cure for one day by moisture. The samples were placed in the test apparatus and burst pressure was recorded in Table V.

(1) Control-A Commercially available DERMABOND® Topical Skin Adhesive (without DIMPTS, without hydroquinone, without sulfur dioxide, without additional heat sterilization) were coated on 5 latex films at a thickness of approximately 0.2 mm. These films were moisture cured without any initiator.
(2) Control-B: Commercially available DERMABOND® Topical Skin Adhesive (without DIMPTS, without hydroquinone, without sulfur dioxide, without additional heat sterilization) were coated on 5 latex films at a thickness of approximately 0.2 mm. The substrate was first coated with an initiator (5% solution of tri-ethyl amine in acetyl tri-butyl citrate) applied from a towelette.
(3) Composition-C: Commercially available DERMABOND® Topical Skin Adhesive (with 2834 ppm DIMPTS, 438 ppm hydroquinone, 250 ppm sulfur dioxide, and with additional heat sterilization) were coated on 5 latex films at a thickness of approximately 0.2 mm. These films were moisture cured without any initiator.
(4) Composition-D: Commercially available DERMABOND® Topical Skin Adhesive (with 2834 ppm DIMPTS, 438 ppm hydroquinone, 250 ppm sulfur dioxide, and with additional heat sterilization) were coated on 5 latex films at a thickness of approximately 0.2 mm. The substrate was first coated with an initiator (5% solution of tri-ethyl amine in acetyl tri-butyl citrate) applied from a towelette.

The burst test result and cure speed observation on all the samples (control and composition) are summarized in Table V (A) and V(B), respectively.

TABLE V(A)

Burst Strength (psi) and Visual Observation of Moisture Activated Curing

| Sample 20 A and C | Burst Strength (psi) (Moisture activated) (n = 5) |
|---|---|
| Control A | 13.5 psi |
| Composition C | 13.8 psi |

TABLE V(B)

Burst Strength (psi) and Visual Observation of Amine Activated Curing

| Sample 20 B and D | Visual Observation of Curing (Amine activated) |
|---|---|
| Control B | 30–45 seconds |
| Composition D | 30–45 seconds |

Table V (A)-(B) indicates that a monomer formulation containing 2834 ppm diiodomethyl-p-tolylsulfone polymerizes to form a polymeric film that demonstrated comparable mechanical strength to a polymeric film formed from the control sample, under either moisture or initiator curing conditions.

What is claimed is:

1. A heat sterilized, antimicrobial formulation having a pre-sterilized cyanoacrylate monomer content for forming a wound closure adhesive comprising:
cyanoacrylate monomer having a post-sterilization content of at least 80% by mole of the pre-sterilized content and diiodomethyl-p-tolylsulfone, wherein the formulation has a viscosity of less than 500 centipoise as measured by a Brookfield viscosimeter at 25° C.

2. The formulation of claim 1 wherein the concentration of said diiodomethyl-p-tolylsulfone is (wt./wt.) between about 500 ppm and about 10,000 ppm.

3. The formulation of claim 2 wherein said concentration of said diiodomethyl-p-tolylsulfone is between about 2,500 ppm and about 7000 ppm.

4. The formulation of claim 1 wherein said cyanoacrylate monomer is selected from the group consisting of 2-octyl cyanoacrylate, n-octyl cyanoacrylate, 2-ethyl hexyl cyanoacrylate, butyl cyanoacrylate and isomers thereof.

5. A method for closing the approximated edges of a wound with a polymeric film that substantially inhibits the growth of microorganisms comprising:
applying a formulation according to claim 1 comprising a cyanoacrylate monomer and diiodomethyl-p-tolylsulfone to the approximated edges of the wound; and allowing the formulation to polymerize to form a polymeric film.

6. A method for preparing a formulation comprising:
a) combining cyanoacrylate monomer and diiodomethyl-p-tolylsulfone into a mixture having an initial cyanoacrylate monomer content; and
b) subjecting the mixture to either heat sterilization temperature of 160° C. for 65 minutes or a gamma sterilization at a dose of 15-20 kGy;
to produce a formulation having at least 80% by mole of the initial cyanoacrylate monomer content.

7. The method of claim 6 wherein said cyanoacrylate monomer is selected from the group consisting of 2-octyl cyanoacrylate, n-octyl cyanoacrylate, 2-ethyl hexyl cyanoacrylate, butyl cyanoacrylate and isomers thereof.

* * * * *